United States Patent
Martin et al.

(10) Patent No.: US 7,323,162 B2
(45) Date of Patent: Jan. 29, 2008

(54) AQUEOUS COSMETIC COLORING AND GLOSS COMPOSITIONS HAVING FILM FORMERS

(75) Inventors: Shari R. Martin, Suffern, NY (US); Giovana A. Sandstrom, North Bergen, NJ (US); Jason N. Rothouse, New City, NY (US); Glen T. Anderson, Pleasantville, NY (US); Alan Letton, Morristown, NJ (US); Hung-Ta Lin, Rego Park, NY (US); Tao Zheng, Nanuet, NY (US)

(73) Assignee: Avon Products, Inc., New York, NY (US)

( * ) Notice: Subject to any disclaimer, the term of this patent is extended or adjusted under 35 U.S.C. 154(b) by 792 days.

(21) Appl. No.: 10/331,184

(22) Filed: Dec. 27, 2002

(65) Prior Publication Data

US 2004/0126346 A1    Jul. 1, 2004

(51) Int. Cl.
*A61K 8/18* (2006.01)
(52) U.S. Cl. .................................................. 424/64
(58) Field of Classification Search ............. 424/401, 424/64, 70.7, 78.02
See application file for complete search history.

(56) References Cited

U.S. PATENT DOCUMENTS

| | | | |
|---|---|---|---|
| 4,792,444 A * | 12/1988 | Fukasawa et al. | 424/63 |
| 4,795,631 A | 1/1989 | Sheehan | 424/64 |
| 5,061,481 A * | 10/1991 | Suzuki et al. | 424/63 |
| 5,100,658 A | 3/1992 | Bolch, Jr. et al. | 424/70 |
| 5,104,646 A | 4/1992 | Bolich, Jr. et al. | 424/70 |
| 5,106,609 A | 4/1992 | Bolich, Jr. et al. | 424/70 |
| 5,219,560 A * | 6/1993 | Suzuki et al. | 424/63 |
| 5,505,937 A | 4/1996 | Castrogiovanni et al. | 424/64 |
| 5,700,898 A | 12/1997 | Okada et al. | 528/25 |
| 5,725,845 A | 3/1998 | Krog et al. | 424/64 |
| 5,800,816 A | 9/1998 | Brieva et al. | 424/64 |
| 5,837,223 A | 11/1998 | Barone et al. | 424/64 |
| 5,843,881 A * | 12/1998 | Dubois et al. | 512/1 |
| 5,846,551 A | 12/1998 | DaCunha et al. | 424/401 |
| 5,849,275 A | 12/1998 | Calello et al. | 424/64 |
| 5,911,974 A | 6/1999 | Brieva et al. | 424/64 |
| 5,945,092 A | 8/1999 | Krog et al. | 424/64 |
| 5,965,112 A | 10/1999 | Brieva et al. | 424/64 |
| 5,972,354 A | 10/1999 | De la Poterie et al. | 424/401 |
| 5,997,889 A * | 12/1999 | Durr et al. | 424/401 |
| 6,033,650 A | 3/2000 | Calello et al. | 424/64 |
| 6,036,947 A | 3/2000 | Barone et al. | 424/64 |
| 6,045,782 A | 4/2000 | Krog et al. | 424/64 |
| 6,071,503 A | 6/2000 | Drechsler et al. | 424/64 |
| 6,074,654 A | 6/2000 | Drechsler et al. | 424/401 |
| 6,113,925 A | 9/2000 | De la Poterie | 424/401 |
| 6,139,823 A | 10/2000 | Drechsler | 424/64 |
| 6,143,283 A | 11/2000 | Calello et al. | 424/64 |
| 6,180,123 B1 | 1/2001 | Mondet | 424/401 |
| 6,224,851 B1 | 5/2001 | Bara | 424/59 |
| 6,254,876 B1 | 7/2001 | De la Poerie et al. | 424/401 |
| 6,254,877 B1 * | 7/2001 | De La Poterie et al. | 424/401 |
| 6,274,152 B1 | 8/2001 | Brieva et al. | 424/401 |
| 6,326,013 B1 | 12/2001 | Lemann et al. | 424/401 |
| 6,338,839 B1 | 1/2002 | Auguste et al. | 426/64 |
| 6,340,466 B1 | 1/2002 | Drechsler et al. | 424/401 |
| 6,395,263 B1 | 5/2002 | Nichols et al. | 424/64 |
| 6,500,439 B1 * | 12/2002 | Morita et al. | 424/401 |
| 6,630,133 B1 * | 10/2003 | Dupuis | 424/70.1 |

FOREIGN PATENT DOCUMENTS

| | | |
|---|---|---|
| JP | 61-289009 | 6/1985 |
| JP | 02-025411 | 1/1990 |
| JP | 02-132141 | 5/1990 |
| JP | 02-250812 | 10/1990 |
| JP | 02-258709 | 10/1990 |
| JP | 04-210613 | 7/1992 |
| JP | 06-279232 | 10/1994 |
| JP | 07-187951 | 7/1995 |
| JP | 07-267817 | 10/1995 |
| JP | 09-143023 | 6/1997 |
| JP | WO 98/55078 | 12/1998 |
| JP | 11-322543 | 11/1999 |
| JP | 2000-327528 | 11/2000 |
| JP | 2001-97814 | 4/2001 |
| JP | 2001-226222 | 8/2001 |
| JP | 2001-278732 | 10/2001 |
| JP | 2002-003333 | 1/2002 |

OTHER PUBLICATIONS

Fedors, "A method for estimating both the solubility parameters and molar volumes of liquids." Polymer Engineering Science, Feb. 1974, vol. 14, No. 2.

Fedors, "A method for estimating both the solubility parameters and molar volumes of liquids." Supplement. Polymer Engineering and Science, Jun. 1974, vol. 14, No. 6, pp. 472.

Bicerano, "Prediction of Polymer Properties." Marcel Dekker, Inc., New York, 1996, pp. 108-136.

Bassett, "Hydrophobic coatings from emulsion polymers." J. of Coatings Tech., vol. 73, No. 912, Jan. 2001, pp. 43-55.

* cited by examiner

*Primary Examiner*—Sharon E. Kennedy
(74) *Attorney, Agent, or Firm*—Ohlandt, Greeley, Ruggiero & Perle, L.L.P.

(57) ABSTRACT

There is provided an aqueous cosmetic composition. The composition has an amount of a water-resistant film former and an amount of an oil-resistant film former effective to impart resistance to both water and oil when applied to the lip and/or skin. A preferred composition is a lip coloring and gloss product.

28 Claims, No Drawings

AQUEOUS COSMETIC COLORING AND GLOSS COMPOSITIONS HAVING FILM FORMERS

BACKGROUND OF THE INVENTION

1. Field of the Invention

The present invention relates to lip and/or skin coloring compositions. The present invention also relates to lip coloring compositions that are water and oil resistant. The present invention further relates to lip glosses that impart a water and oil resistant cosmetic finish to the lip.

2. Description of the Related Art

Lip compositions are commonly used to impart a cosmetic finish or color to the lip. Conventional lip compositions are semisolid mixtures of waxes, oils, and colorants.

When applied to the lip, lip compositions remain in a semi-solid state. Frequent reapplication is needed to maintain the desired cosmetic appearance, as the lip composition can be worn off in the course of eating, drinking, smoking, or talking.

U.S. Pat. No. 4,795,631 relates to aqueous lip compositions having an alkali-dispersible or alkali-soluble, water-insoluble thermoplastic film-forming resin, a volatile base and a water-insoluble plasticizer. The compositions are disclosed as being flexible, long-wearing, and water-resistant.

U.S. Pat. No. 5,846,551 relates to an aqueous makeup composition having a water-dispersible pigment having a nonionic coating, a lipid vesicle having one or more lipid components, and an aqueous carrier. The composition is described as exhibiting unusual stability at low pH.

It would be desirable to have a lip gloss and/or lip coloring composition that exhibits excellent wear resistance. It would be further desirable to have a lip gloss and/or lip coloring composition that exhibits excellent water and oil resistance.

SUMMARY OF THE INVENTION

It is an object of the present invention to provide stable compositions that exhibit excellent wear resistance on the lip.

It is a further object of the present invention to provide compositions that exhibit excellent water and oil resistance on the lip.

It is a still further object of the present invention to provide compositions that impart a transfer-resistant cosmetic finish to the lip.

According to this and other objects and advantages of the present invention, there are provided aqueous lip compositions and methods for applying same. The compositions have an amount of a water-resistant film former and an amount of an oil-resistant film former effective to impart resistance to both water and oil. A preferred composition is a lip coloring composition. A more preferred composition is a lip coloring and lip gloss composition, most preferably in an emulsion form.

Further according to this and other objects and advantages of the present invention, there are also provided methods for coloring the skin. A method includes applying to the skin a composition having an amount of a water-resistant film former and an amount of an oil-resistant film former effective to impart resistance to both water and oil, and to provide improved gloss.

DETAILED DESCRIPTION OF THE INVENTION

The present invention provides compositions that exhibit excellent wear and transfer resistance, particularly resistance to oil and water on the lip and/or skin. Further, it includes methods for coloring the lip and/or skin by applying one of the compositions thereto.

The composition has an amount of the water-resistant film former effective to impart water resistance to the lip and/or skin. Preferably, the water-resistant film former is present at about 0.1 wt % to about 50 wt % based on the total weight of the composition. More preferably, the water-resistant film former is present at about 1.0 wt % to about 20 wt % based on the total weight of the composition.

The composition has an amount of the oil-resistant film former effective to impart oil resistance to the lip and/or skin. Preferably, the oil-resistant film former is present at about 0.1 wt % to about 50 wt % based on the total weight of the composition. More preferably, the oil-resistant film former is present at about 1.0 wt % to about 20 wt % based on the total weight of the composition.

The combination of the water-resistant film former and the oil-resistant film former is deemed to have a synergistic effect in enhancing the wear and transfer resistance of the lip coloring composition.

Water-resistant film formers and oil-resistant film formers that can be used in the present compositions include, but are not limited to, one or more acrylics (acrylates), polyacrylates, urethanes, polyurethanes, polyesters, polysaccharides, polyolefins, polyamides, polyimides, polyethylenes, polyalkyls, polyols, polystyrenes, polyethers, polyhalides, polynitriles, cellulosics, proteins, triglycerides, polyamino acids, silicone polymers and resins, esters derived from rosin, epoxy resins, shellacs, latexes, or any combinations thereof.

Acrylates and polyacrylates (acrylate polymers) are preferred as both water-resistant film formers and oil-resistant film formers. Although not bound by any particular theory, suitable acrylate polymers may be selected on the basis of their properties and/or structure. Some acrylates are insoluble in water in their free acid form and, thus, are water resistant. If such water-insoluble acrylates are neutralized with a base to their salt form, water solubility is significantly increased. Although increased water solubility may somewhat reduce water resistance, the increased water solubility enhances oil resistance. The solubility profile of an acrylate polymer may be impacted by the incidence of acid groups therein. The higher the incidence of acid groups, the more water soluble the acrylate polymer may be at neutral pH, and, thus, the more it is oil resistant. The lower the incidence of acid groups, the more oil soluble the acrylate polymer may be at neutral pH, and, thus, the more it is water resistant. A particularly desirable acrylate polymer system may have an acrylate polymer with a small incidence of acid groups and a second acrylate polymer with a high incidence of acid groups. Such acrylate polymer system may provide a film forming system that is resistant to both water and oil.

Preferred acrylate and polyacrylate film formers are acrylates copolymers (such as, Covacryl A15 and Covacryl E14 by Wackherr), acrylates/ethylhexyl acrylate copolymers (Daitosol 5000SJ by Daito Kasei), butyl acrylate/hydroxypropyl dimethicone acrylate copolymers (Granacrysil BAS by Grant Industries, Inc.), acrylates/$C_{12}$-$C_{22}$ alkylmethacrylate copolymers (Allianz OPT by ISP), isododecane and acrylates copolymers (Giovarez AC-5099M by Phoenix), acrylates/octylacrylamide copolymers (Dermacryl-79 by National Starch & Chemical Company), and sodium polystyrene sulfonates (Flexan 130 by National Starch & Chemical Company).

For purposes of the present invention, whether a film former is water-resistant or oil resistant is determined according to its Fedor's solubility (solubility parameter) and surface tension value. A water-resistant film former has a solubility parameter about 20 or less and a surface tension value about 30 or less. An oil-resistant film former has a solubility parameter of greater than about 20 and a surface tension value greater than about 30. In this context, "about" means a difference of no more than one unit of measure.

Fedor's solubility (solubility parameter) (δ) is calculated based on the predictive correlations for polymer solubility in water based on its composition with respect to any of the following nine elements: carbon, hydrogen, nitrogen, oxygen, silicon, sulfur, fluorine, chlorine, and bromine.

$$\delta = \sqrt{\frac{E_{coh}}{V}}$$

$$E_{coh} = 9882.5X + 358.7(6N_{atomic} + 5N_{group})$$

wherein $E_{coh}$ is cohesive energy, V is molar volume, X is the first order connectivity index, $N_{atomic}$ is the atomic correction term, and $N_{group}$ is the correction term for underestimation or overestimation of $E_{coh}$.

Teachings to the prediction of Fedor's solubility and use of the Fedor's method are described in Fedors, R. F. *Polym. Eng Sci.* 14, 147, 472 (1974), and Bicerano, J., *Prediction of Polymer Properties*, Marcel Dekker Inc., N.Y. (1993), which are incorporated herein by reference. The Synthia module in Cerius, a molecular software package from Accelrys Inc., was used to calculate solubility parameter.

Surface tension of the film formers is measured by the plate method with a KRUSS processor tensiometer K12. The probe employed is a KRUSS standard platinum plate having a width of 19.9 millimeters (mm), a thickness of 0.2 mm and a height of 10.0 mm. Settings are the following: room temperature, detection speed at 6 mm/minute, immersion depth at 2.0 mm, measurement time at 60 seconds and sensitivity at 0.01 grams.

The compositions of the present invention are aqueous-based. Preferably, water is present at about 10 wt % to about 90 wt % based on the total weight of the composition. More preferably, water is present at about 25 wt % to about 75 wt % based on the total weight of the composition. Even more preferably, water is present at about 30 wt % to about 75 wt % based on the total weight of the composition. Most preferably, water is present at about 50 wt % to about 75 wt % based on the total weight of the composition.

Colorants that can be used in the present compositions include, but are not limited to, D&C Red No. 3, D&C Red No. 6, D&C Red No. 7, D&C Red No. 8, D&C Red No. 9, D&C Red No. 21, D&C Red 22, D&C Red No. 27, D&C Red 28, D&C Red No. 30, D&C Red No. 33, D&C Red 34, D&C Red No. 36, FD&C Red No. 40, D&C Yellow No. 5, FD&C Yellow No. 5, FD&C Yellow No. 6, D&C Yellow No. 10, D&C Green No. 3, D&C Green No. 5, D&C Orange No. 5, FD&C Blue No. 1, annatto, copper powder, bismuth oxychloride, guanine, bronze powder, iron oxides, carmel, manganese violet, carmine, mica, titanium dioxide-coated mica, carotene, titanium dioxide, chlorophyllin-calcium complex, zinc oxide, or any combinations thereof.

The compositions may have other ingredients such as one or more anesthetics, anti-allergenics, antifungals, anti-inflammatories, antimicrobials, antiseptics, chelating agents, emollients, emulsifiers, fragrances, humectants, lubricants, masking agents, medicaments, moisturizers, pH adjusters, preservatives, protectants, soothing agents, stabilizers, sunscreens, surfactants, thickeners, viscosifiers, vitamins, or any combinations thereof.

The composition can take any semisolid or liquid product form suitable for application to the lip and/or skin, such as a cream, ointment, solution, paste, pomade, gel, or lotion. The composition can take any semisolid composition form, such as an emulsion, a suspension, or a dispersion.

A preferred composition is a lip coloring and/or lip gloss product. The lip coloring product must have water, the water-resistant and the oil-resistant film formers, and a colorant. The lip gloss may have additional oils and/or waxes and/or other ingredients to achieve a desired product form, physical consistency and/or shine. The composition may also be a foundation, liner, eyeshadow or mascara product.

The composition can be applied as often as necessary to impart the desired cosmetic finish, color or appearance to the lip and/or skin. The lip coloring and lip gloss products preferably imparts a moist feel to the lips. The present invention affords lip coloring and lip gloss products with creamy, smooth and even application. After application, the products dry to an even film on the lips and resist transfer and wear from abrasion. These performance benefits are due to the inclusion of both a water-resistant and an oil-resistant film former. Erosion from drinking, eating, smoking, talking and the like is significantly reduced. The need for reapplication of product is significantly reduced. Typically, a conventional lip gloss will not have such long wear properties.

The following is an example of a composition of the present invention. Unless otherwise indicated, all percentage or parts are by weight.

EXAMPLE

A composition of the present invention was prepared and tested against a control composition lacking the water-resistant and oil-resistant film formers of the present invention. The composition was evaluated for transfer resistance.

First, ingredients were evaluated for suitability as film formers in the composition of the present invention. The ingredients were evaluated or tested for Fedor's solubility and surface tension according to the parameter requirements and techniques disclosed herein. The solubility and surface tension parameters obtained are set forth in Table 1:

TABLE 1

| Ingredient | Solubility $(J/cm^3)^{1/2}$ | Surface Tension (dyne/cm) |
| --- | --- | --- |
| Granacrysil BAS | 16.78 | 15.92 |
| Daitosol 5000 SJ | 19.15 | 39.31 |
| Glovarez AC | 20.54 | 22.12 |
| Covacryl A15 | 20.63 | 26.75 |
| Dermacryl 79 | 20.99 | 32.98 |
| Covacryl E14 | 21.26 | 40.08 |
| Flexan 130 | 25.05 | 36.25 |
| Allianz OPT | 18.34 | 48.23 |
| Performa V825 | 17.43 | 32.32 |

$J/cm^3$ = Joules/cubic centimeter
Covacryl A15 / Covacryl E14 = acrylates copolymer (Wackherr)
Daitosol 5000SJ = acrylates/ethylhexyl acrylate copolymer (Daito Kasei)
Granacrysil BAS = butyl acrylate/hydroxypropyl dimethicone acrylate copolymer (Grant Industries, Inc.)
Giovarez AC-5099M = isododecane and acrylates copolymer (Phoenix)
Dermacryl-79 = acrylates/octylacrylamide copolymer (National Starch & Chemical Company)
Flexan 130 = sodium polystyrene sulfonate (National Starch & Chemical Company)
Allianz OPT - Acrylates/$C_{12}$-$C_{22}$ Alkylmethacrylate Copolymer (ISP)
Performa V825 = Synthetic Wax (New Phase)

The composition of the present invention (Formula B) and the control composition (Formula A) were prepared as described below.

In a first vessel, under high sheer, Bentone RV is dispersed into the water at room temperature. The remaining water-soluble materials are slowly added and mixed under high sheer until homogeneously dispersed.

In a second vessel, phenyl trimethicone, castor isostearate succinate, dimethicone, sucrose acetate isobutyrate, and other oil soluble ingredients of Phase B of the following formula, are blended together until homogeneous at room temperature, at which time colorants are slowly added under high sheer until uniformly dispersed.

The water-soluble blend from the first vessel is slowly poured into the second vessel under continuous high sheer mixing at room temperature. High sheer mixing continues for 5-10 minutes, at which time the composition is fully constituted.

The content of the composition of the present invention is as follows:

| Name | Wt. % A | Wt. % B |
|---|---|---|
| Phase A (water) | | |
| Demineralized Water | 31.47 | 31.47 |
| Bentone RV | 1.11 | 1.11 |
| Covacryl A15 | xxxxxx | 15.36 |
| Covacryl E14 | xxxxxx | 9.22 |
| Covaplast | 7.68 | 7.68 |
| Daitosol 5000 SJ | xxxxxx | 7.3 |
| Liquipar Optima | 0.76 | 0.76 |
| Talc FS Treated 1.6% | 1.54 | 1.54 |
| Allianz OPT | 10.83 | xxxxxx |
| Phase B (oil) | | |
| Phenyl Trimethicone | 0.5 | 0.5 |
| Castor Isostearate Succinate | 2.12 | 2.12 |
| Dimethicone | 20.48 | 3 |
| Dow 9040 Elastomer | 0.64 | 0.64 |
| Dow 5225C Formulation Aid | 2 | 2 |
| Sucrose Acetate Isobutyrate (SAIB) | 5.9 | 5.9 |
| Granacrysil BAS | xxxxxx | 3.9 |
| Performa V 825 | 7.47 | xxxxxx |
| Diisostearyl Fumarate | 1.84 | 1.84 |
| Etoxydiglycol Oleate | 1.84 | 1.84 |
| D&C Red # 21 | 0.06 | 0.06 |
| TiO2 / Dm/Glycerol Rosinate | 2.81 | 2.81 |
| Black IO/Dm/Gly Rosinate | 0.13 | 0.13 |
| Red IO /Dm/Gly Rosinate | 0.5 | 0.5 |
| D&C Red 7/Dm/ Glycerol Rosinate | 0.28 | 0.28 |
| Barium Sulfate | 0.04 | 0.04 |
| Total: | 100 | 100 |

As the skilled artisan will note, Formulas A and B are identical, except for the difference in film former materials. In particular, Formula B (the Invention) uses Covacryl A15 (30% Active), Covacryl E14 (30% active), Daitosol 5000 SJ (50% active) and Granacrylsil BAS (100% active), for a total film-former concentration of 14.93%. Each of these film-formers meets the limitation of the present invention. Formula A (the Control) uses Allianz OPT (45% active) and Performa V825 (100% active), for a total film-former concentration of 14.93%. Both of the control film-formers are outside the limitations of the present invention.

The compositions were then evaluated for transfer resistance. In the procedure for evaluating transfer resistance, a small sheet of casein was hydrated for at least two hours at 90% relative humidity and then attached to a glass plate. A thin, uniform film of the cosmetic composition was applied to the hydrated casein and allowed to dry for two hours at ambient conditions. A round polystyrene foam disk was attached to a 2 kilogram weight. Droplets of water (or vegetable oil) were placed on the cosmetic film, and the weighted plastic foam disk was placed on the film and rotated. The weight was then lifted and the percent reflectance of the polystyrene foam disk was measured. The measurement was taken using the Gretag Macbeth Color Eye XTH using the Optiview Propalette version 2.0 f over the wavelength 400 nm to 700 nm.

The results of the transfer resistance tests are set forth below:

| | INVENTION (B) | CONTROL (A) |
|---|---|---|
| REFLECTANCE-Water | 74% | 0% |
| REFLECTANCE-Oil | 84% | 0.1% |
| AVERAGE GROSS | 29.1% | 24.8% |

The percentages correspond to the color reflectance on the foam disk as compared to a blank or clean foam disk. The more product transferred to the disk, the lower the percentage reflectance. The higher the percentage reflectance, the higher the transfer resistance.

The composition of the present invention (Formula B) exhibited high levels of transfer resistance to both water and oil. The control composition (Formula A) exhibited poor to no transfer resistance for both water and oil. The composition of the present invention also provided improved gloss.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A cosmetic composition, comprising:
   10 wt % to about 90 wt % water; and
   an amount of a water-resistant film former and an amount of an oil-resistant film former effective to impart water and oil resistance to the composition, wherein the water-resistant film former is a butyl acrylate/hydroxypropyl dimethicone acrylate copolymer, and wherein the oil-resistant film former is an acrylates copolymer.

2. The composition of claim 1, further comprising a colorant.

3. The composition of claim 1, wherein the composition is a lip gloss.

4. The composition of claim 1, wherein the composition is a lip coloring composition.

5. The composition of claim 1, wherein the composition is selected from the group consisting of a foundation, an eyeshadow, a liner and a mascara.

6. The composition of claim 1, wherein the water-resistant film former is present at about 0.1 wt % to about 50 wt % based on the total weight of the composition.

7. The composition of claim 1, wherein the water-resistant film former is present at about 1 wt % to about 20 wt % based on the total weight of the composition.

8. The composition of claim 1, wherein the water-resistant film former has a Fedor's solubility value about 20 or less and a surface tension value about 30 less.

9. The composition of claim 1, wherein the oil-resistant film former is present at about 0.1 wt % to about 50 wt % based on the total weight of the composition.

10. The composition of claim 1, wherein the oil-resistant film former is present at about 2 wt % to about 20 wt % based on the total weight of the composition.

11. The composition of claim 1, wherein the oil-resistant film former has a Fedor's solubility value greater than about 20 and a surface tension value greater than about 30.

12. The composition of claim 1, wherein the water is present at about 25 wt % to about 75 wt % based on the total weight of the composition.

13. The composition of claim 2, wherein the colorant is present at about 0.1 wt % to about 20 wt % based on the total weight of the composition.

14. The composition of claim 1, further comprising about 0.1 wt % to about 10 wt % of a colorant, wherein the composition is a lip coloring composition, and wherein the water-resistant film former is present at about 1 wt % to about 20 wt %, and wherein the oil-resistant film former is present at about 1 wt % to about 20 wt %, and wherein the water is present at about 25 wt % to about 75 wt % based on the total weight of the composition.

15. A method of imparting transfer-resistant color and/or gloss to lips and/or skin, comprising applying to the lips and/or skin & composition having 10 wt % to about 90 wt % water; and an amount of a water-resistant film former and an amount of an oil-resistant film former effective to impart resistance to both water and oil when applied to the lips and/or skin, wherein the water-resistant film former is a butyl acrylate/hydroxypropyl dimethicone acrylate copolymer, and wherein the oil-resistant film former is an acrylates copolymer.

16. The method of claim 15, wherein the composition has a colorant.

17. The method of claim 16, wherein the composition is a lip gloss.

18. The method of claim 16, wherein the composition is a lip coloring composition.

19. The method of claim 16, wherein the composition is selected from the group Consisting of a foundation, an eyeshadow, a liner and a mascara.

20. The method of claim 15, wherein the water-resistant film former is present at about 0.1 wt % to about 50 wt % based on the total weight of the composition.

21. The method of claim 15, wherein the water-resistant film former is present at about 1 wt % to about 20 wt % based on the total weight of the composition.

22. The method of claim 15, wherein the water-resistant film former has a Fedor's solubility value about 20 or less and a surface tension value about 30 less.

23. The method of claim 15, wherein the oil-resistant film former is present at about 0.1 wt % to about 50 wt % based on the total weight of the composition.

24. The method of claim 15, wherein the oil-resistant film former is present at about 1 wt % to about 20 wt % based on the total weight of the composition.

25. The method of claim 15, wherein the oil-resistant film former has a Fedor's solubility value greater than about 20 and a surface tension value greater than about 30.

26. The method of claim 15, wherein the water is present at about 25 wt % to about 75 wt % based on the total weight of the composition.

27. The method of claim 15, wherein the colorant is present at about 0.1 wt % to about 20 wt % based on the total weight of the composition.

28. The method of claim 15, wherein the composition has about 0.1 wt % to about 10 wt % of a colorant, wherein the composition is a lip coloring composition, and wherein the water-resistant film former is present at about 1 wt % to about 20 wt %, and wherein the oil-resistant film former is present at about 1 wt % to about 20 wt %, and wherein the water is present at about 25 wt % to about 75 wt % based on the total weight of the composition.

* * * * *